United States Patent [19]

Schoebrechts et al.

[11] Patent Number: 5,821,394
[45] Date of Patent: Oct. 13, 1998

[54] PROCESS FOR CONVERTING A CHLORINATED ALKANE INTO A LESS CHLORINATED ALKENE

[75] Inventors: Jean-Paul Schoebrechts, Grez-Doiceau; Francine Janssens, Vilvoorde, both of Belgium

[73] Assignee: Solvay, Brussels, Belgium

[21] Appl. No.: 836,782

[22] PCT Filed: Nov. 15, 1995

[86] PCT No.: PCT/EP95/04516

§ 371 Date: May 16, 1997

§ 102(e) Date: May 16, 1997

[87] PCT Pub. No.: WO96/16003

PCT Pub. Date: May 30, 1996

[30] Foreign Application Priority Data

Nov. 24, 1994 [FR] France .................................. 94 14203
Sep. 20, 1995 [FR] France .................................. 95 11131

[51] Int. Cl.⁶ ............................ C07C 17/25; C07C 21/04
[52] U.S. Cl. ............................ 570/227; 585/642; 585/641
[58] Field of Search ............................ 570/227; 585/612, 585/620, 627, 629, 890, 641, 642; 208/262.1

[56] References Cited

U.S. PATENT DOCUMENTS

| | | |
|---|---|---|
| 3,892,818 | 7/1975 | Scharfe et al. . |
| 5,453,557 | 9/1995 | Harley et al. ............................ 585/641 |
| 5,476,979 | 12/1995 | Ito et al. ................................. 585/641 |
| 5,498,806 | 3/1996 | Ichikawa et al. ...................... 570/156 |
| 5,637,548 | 6/1997 | Ito et al. ................................. 502/330 |

FOREIGN PATENT DOCUMENTS

| | | |
|---|---|---|
| 0640574 | 3/1995 | European Pat. Off. . |
| 94/07818 | 4/1994 | WIPO . |
| 94/07819 | 4/1994 | WIPO . |
| 94/07820 | 4/1994 | WIPO . |
| 94/07821 | 4/1994 | WIPO . |
| 94/07823 | 4/1994 | WIPO . |
| 94/07827 | 4/1994 | WIPO . |
| 94/07828 | 4/1994 | WIPO . |

*Primary Examiner*—Bekir L. Yildirim
*Attorney, Agent, or Firm*—Spencer & Frank

[57] ABSTRACT

Process for converting a chlorinated alkane into at least one less chlorinated alkene by reaction with hydrogen in the presence of a catalyst comprising palladium and a metal selected from the group consisting of silver, gallium, indium, thallium, germanium, tin, lead, arsenic, antimony, bismuth and mixtures thereof.

18 Claims, No Drawings

PROCESS FOR CONVERTING A CHLORINATED ALKANE INTO A LESS CHLORINATED ALKENE

This application is a 371 of PCT/EP95/04516, filed Nov. 15, 1995.

The invention relates to a process for converting a chlorinated alkane into at least one less chlorinated alkene by reacting the chlorinated alkane with hydrogen in the presence of a catalyst comprising a metal from group VIII and another metal on a support.

TECHNOLOGY REVIEW

International applications WO-94/07828, WO-94/07827, WO-94/07823, WO-94/07821, WO-94/07820, WO-94/07819, and WO-94/07818 describe processes for converting various chlorinated alkanes into less chlorinated alkenes by means of hydrogen in the presence of a bimetallic catalyst comprising a metal from group VIII and a metal from group IB which are deposited on a support. European Patent Application EP-A-0 640 574 describes the conversion of chlorinated alkanes into less chlorinated alkenes in the presence of a bimetallic catalyst comprising platinum and a second metal, such as lanthanum, titanium, vanadium, chromium, manganese, iron, cobalt, nickel, copper, zinc, indium, tin or bismuth, on a support. In these known processes, the best degrees of conversion of the chlorinated alkanes and the best selectivities as regards the production of alkenes are obtained with the bimetallic catalyst platinum-copper on active charcoal. International Application WO-94/07819 and European Patent Application EP-A-0 640 574 describe more specifically processes for converting 1,2-dichloropropane into propylene. It is evident therefrom that the bimetallic catalysts specified above do not make it possible to obtain both a high degree of conversion of 1,2-dichloropropane and a high selectivity for propylene. Moreover, these catalysts are initially of very low selectivity with respect to the formation of propylene, with a large quantity of propane being produced. Because of this, these known catalysts are unsuitable for generating propylene which can be used directly in a unit for the production of allyl chloride by chlorination of propylene. In effect, when a mixture comprising propylene and propane is recycled to the allyl chloride production stage, 1-chloropropane and/or 2-chloropropane are formed by chlorination of propane, and these products are difficult to separate from the allyl chloride. Another disadvantage of these known catalysts is their rapid deactivation. Consequently, the pretreatment of these catalysts using hydrogen chloride is necessary in order to improve their initial selectivity and their stability. The patent U.S. Pat. No. 3,892,818 discloses a process for de-chlorinating 1,2-dichloropropane using hydrogen in the presence of a bimetallic rhodium-gold catalyst supported on alumina. This catalyst has a good activity and a long life, but the reaction product is essentially propane.

SUMMARY OF THE INVENTION

A process has now been found which does not have the above-described disadvantages and which makes it possible to convert chlorinated alkanes into less chlorinated alkenes with a good selectivity and preferably with a high degree of conversion without the catalyst either becoming rapidly deactivated over time or requiring pretreatment with hydrogen chloride.

The invention consequently relates to a process for converting a chlorinated alkane into at least one less chlorinated alkene by reacting the chlorinated alkane with hydrogen in the presence of a catalyst comprising a metal from group VIII and a metal M, on a support, which is characterized in that the metal from group VIII is palladium and the metal M is selected from the group consisting of silver, gallium, indium, thallium, germanium, tin, lead, arsenic, antimony, bismuth and mixtures thereof.

DETAILED DESCRIPTION OF THE INVENTION

The chlorinated alkane employed in the process according to the invention is an alkane comprising at least one chlorine atom. Good results have been obtained with acyclic chlorinated alkanes and, more especially, with acyclic chlorinated alkanes of general formula $C_nH_{2n+2-x}Cl_x$ in which n is an integer from 2 to 6 and x is an integer from 1 to (2n+2). Chloropropanes are particularly advantageous, and dichloropropanes and trichloropropanes are more especially so. 1,2-dichloropropane is very particularly advantageous.

The term less chlorinated alkene is intended to denote an alkene in which the number of carbon atoms corresponds to the number of carbon atoms of the chlorinated alkane employed and which has at least one chlorine atom less than the chlorinated alkane employed. The less chlorinated alkene as defined in the present invention may therefore contain no chlorine atoms. In the case of a chlorinated alkane of general formula $C_nH_{2n+2-x}Cl_x$ in which x=1 to (2n+2), the alkene formed in the process according to the invention therefore corresponds to the general formula $C_nH_{2n-y}Cl_y$ in which y varies from 0 to 2n, without being higher than (x−1). In the process according to the invention, the reaction of the chlorinated alkane with hydrogen may produce a single less chlorinated alkene as defined above or a mixture of two or more less chlorinated alkenes.

The catalyst employed in the process according to the invention comprises palladium and at least one metal M selected from the group consisting of silver, gallium, indium, thallium, germanium, tin, lead, arsenic, antimony and bismuth, on a support. The metal M is preferably selected from silver, tin, lead, thallium and bismuth. Good results have been obtained when the metal M is tin. Excellent results have been obtained when the metal M is silver. The catalyst preferably consists essentially of palladium and a metal M on the support. The palladium and the metal M may be in the elemental state or in the form of a compound, such as a salt or an oxide. The catalyst preferably comprises palladium and the metal M in the elemental state.

As catalyst support, use is commonly made of a porous support such as those which are currently used with the catalysts employed in hydrogenation reactions. Examples of such supports are active charcoal, alumina, silica, titanium oxide, magnesium oxide, zirconium oxide, lithium aluminate and silica-alumina. The preferred support is active charcoal.

The quantity of palladium on the support is advantageously at least 0.05%, preferably at least 0.15%, by weight relative to the weight of the support. Commonly, the quantity of palladium does not exceed 10% by weight relative to the weight of the support. Preferably it does not exceed 5%.

The quantity of metal M on the support is advantageously at least 0.05%, preferably at least 0.15%, by weight relative to the weight of the support. Commonly, the quantity of this metal M does not exceed 10% by weight relative to the weight of the support. Preferably it does not exceed 5%.

The ratio by weight of the palladium to the metal M is preferably at least 0.05. It is particularly preferred for this ratio by weight to be at least 0.1. It is more particularly preferred for this ratio by weight to be at least 0.25. Preferably, the ratio by weight of the palladium to the metal M does not exceed 20. It is particularly preferred for this ratio not to exceed 10. It is more particularly preferred for this ratio not to exceed 4.

In a specific embodiment of the process according to the invention, in which the metal M is silver, the weight ratio of palladium to silver is very particularly preferably at least 0.4. In this embodiment of the invention, the weight ratio of palladium to silver preferably does not exceed 2.5.

The catalyst may additionally, if appropriate, comprise at least one additional metal which is selected from metals from group IB, IIB, IIIA, IVA, VA and VIII, in the elemental stage or in the form of a compound of this metal (the groups are designated in accordance with the CAS nomenclature as reproduced in the CRC Handbook of Chemistry and Physics, 75th edition, 1994–1995, D. R. Lide, cover page). If appropriate, the quantity of this additional metal does not exceed 50% by weight of the overall weight of palladium and the metal M.

The metals of the catalyst employed in the process according to the invention can be deposited on the support by impregnating the latter with one or more solutions containing the metal constituents of the catalyst. The impregnating solutions are preferably aqueous salt solutions. The salts used for this purpose are, in particular, chlorides, nitrates, acetates or ammonia complexes. According to a preferred variant of the process according to the invention, a catalyst is employed which is obtained by two successive impregnations. In this case, the support is first of all impregnated with a solution comprising palladium, dried, then impregnated with a solution comprising the metal M, and dried again. Commonly, the impregnated and dried support is subjected to heat treatment in a reducing atmosphere such as, for example, hydrogen at a temperature of at least 100° C. and preferably less than or equal to 400° C. The heat treatment of the impregnated support can be carried out prior to the use of the catalyst in the process or at the same time as the chlorinated alkane and hydrogen are employed in the process.

In the process according to the invention, the molar ratio of hydrogen to chlorinated alkane is preferably at least 0.1, more particularly at least 0.5. This ratio preferably does not exceed 40. With particular preference, it does not exceed 20.

In the process according to the invention, the hydrogen reacts with the chlorinated alkane to produce at least one less chlorinated alkene, as set out above. The hydrogen can if appropriate be mixed with another gas, which is inert under the reaction conditions of conversion of the chlorinated alkane into less chlorinated alkene. The other gas used may be a gas from the group of the inert gases proper, such as helium, or a gas which does not intervene in the abovementioned reaction, such as hydrochloric acid or an alkene. In the case where the inert gas selected is an alkene, it is preferably the alkene or one of the alkenes formed by the reaction of the chlorinated alkane with hydrogen. The fraction by volume of hydrogen is preferably at least 5% of the total volume of hydrogen and the other gas. With particular preference, the hydrogen fraction is at least 10% of the total volume.

The process according to the invention can be carried out in liquid phase or in gaseous phase. The process according to the invention is preferably performed in the gaseous phase. The process takes place preferably at a temperature of at least 150° C., more particularly at least 200° C. The temperature generally does not exceed 450° C. Preferably it does not exceed 400° C. The pressure at which the process is carried out is not critical per se. Generally, a pressure of at least 1 bar is employed. In general, the pressure does not exceed 30 bar. Preferably it does not exceed 10 bar.

In the case where the process according to the invention is carried out in the gaseous phase, the mean contact time between the gases employed and the catalyst, i.e. the ratio between the volume occupied by the catalyst and the total feed flow rate, measured at the temperature and pressure of the reaction, is preferably at least 0.5 second, more particularly at least 1 second. The contact time preferably does not exceed 30 seconds. With particular preference, the contact time does not exceed 20 seconds.

The process according to the invention makes it possible to obtain a high degree of conversion of the chlorinated alkane and a very large selectivity for less chlorinated alkene. The process according to the invention additionally makes it possible to obtain a good selectivity for the less chlorinated alkenes, without any notable formation of alkanes or chlorinated alkanes, and it achieves these advantages right from the moment when the catalyst is first employed and without pretreatment of the catalyst with hydrogen chloride. The process according to the invention, moreover, has the advantage that deactivation of the catalyst over time is particularly slow compared with the deactivation of known catalysts from the prior art.

In the specific case where the chlorinated alkane employed in the process according to the invention is 1,2-dichloropropane, propylene is obtained with a good selectivity and a good degree of conversion. The invention therefore relates in particular to a process for obtaining propylene by reacting 1,2-dichloropropane with hydrogen in the presence of a catalyst comprising palladium and a metal M selected from the group consisting of silver, gallium, indium, thallium, germanium, tin, lead, arsenic, antimony, bismuth and mixtures thereof on a support.

The process according to the invention finds very advantageous application in the conversion of chloropropanes, and more particularly of chloropropanes which are formed as by-products in the production of allyl chloride by chlorination of propylene and/or in the production of epichlorohydrin by hypochlorination of allyl chloride. Particular examples of chloropropanes which are by-products in these production processes are 1,2-dichloropropane and 1,2,3-trichloropropane. The chloropropanes employed in this application of the process according to the invention may contain a small quantity, generally less than 5% by weight, of other products, especially products which occur in the production of allyl chloride and/or of epichlorohydrin, and more particularly chloropropenes, such as 1,3-dichloropropene, 2-chloropropene and allyl chloride. This particular application of the process according to the invention is particularly advantageous since it makes it possible to obtain propylene which contains only a very small quantity of propane, generally less than 3% and most frequently less than 1%, which can thus be recycled directly to the stage of production of allyl chloride by chlorination of propylene. The use in the allyl chloride production stage of a propylene of low propane content makes it possible to limit the quantity of 1-chloropropane and/or 2-chloropropane which are formed by chlorination of propane and which are difficult to separate from allyl chloride.

EXAMPLES

The invention is illustrated more fully by the following examples.

Example 1 (in accordance with the invention)

In this example, a Pd-Ag catalyst was employed on a support of active charcoal.
a) Preparation of the catalyst on the support 10 g of active charcoal (grade NC 35 sold by the company CECA) having a pore volume of 0.5 ml/g were introduced into a round-bottomed flask with 3.5 ml of water and 1.5 ml of a solution containing 0.10 g Pd/ml (solution of $PdCl_2$ in 6N HCl). After a period of 15 minutes at room temperature, the impregnated active charcoal was dried under vacuum at 80° C. After cooling to room temperature, 6 ml of a solution containing 0.05 g of Ag/ml (AgCl in an aqueous ammonia solution containing 25% by weight of $NH_3$) were introduced into the flask. After a period of 15 minutes at room temperature, the impregnated active charcoal was dried initially under vacuum at 80° C. and then under a helium atmosphere for 1 h at 120° C. and for 1 h at 280° C. The impregnated and dried active charcoal was then treated at 280° C. for 4 h with hydrogen. The catalyst thus obtained comprised 1.5% by weight of Pd and 3% of Ag relative to the weight of active charcoal employed. X-ray diffraction analysis of the catalyst showed that the metals were in part present in the form of alloys comprising between 20 and 50 atom % of silver, the particle size being from 3 to 10 nm.

b) Conversion of 1,2-dichloropropane 3.43 g (7.50 cm³) of the catalyst described above were introduced into a reaction tube (internal diameter=0.8 cm). The reactor containing the catalyst was then fed continuously at a rate of 2.6 l/h (s.t.p.) with 1,2-dichloropropane and with 10.3 l/h (s.t.p.) of hydrogen at 345° C. under 1.5 bar for several hours. The residence time was assessed as being 1.39 s.

At various intervals of time, a sample of the products continuously leaving the reactor was taken and was analysed by gas chromatography, and the degree of conversion of 1,2-dichloropropane and the selectivity for propylene (defined as the molar fraction of 1,2-dichloropropane reacted which has been converted to propylene) were measured. The results of the measurements are reproduced in Table I. This table shows that, after more than 150 h of operation, the catalyst is still as active and selective as at the beginning. After approximately 8 days of operation, the catalyst still makes it possible to obtain a degree of conversion of greater than approximately 95%. At this time, approximately 711 kg of 1,2-dichloropropane have been converted per kg of catalyst.

Example 2 (not in accordance with the invention)

1,2-dichloropropane was converted under the same operating conditions as those described in Example 1, but using 3.67 g (7.50 cm³) of a catalyst comprising 2.7% by weight of Pt and 1.8% by weight of Cu relative to the weight of active charcoal. This catalyst was applied to the same support and under the same operating conditions as in Example 1, using aqueous solutions of $H_2PtCl_6 \cdot 6H_2O$ and $CuCl_2 \cdot 2H_2O$.

After various intervals of time, the degree of conversion of 1,2-dichloropropane and the selectivity for propylene were measured as in Example 1. The results of these measurements are likewise reproduced in Table I.

TABLE I

|  | EXAMPLE 1 (1.5% Pd-3.0% Ag) | | EXAMPLE 2 (2.7% Pt-1.8% Cu) | |
|---|---|---|---|---|
| DURATION (h) | conversion % | selectivity mol % | conversion % | selectivity mol % |
| 0.50 | 99.80 | 87.12 | 99.96 | 80.69 |
| 3.50 | 99.93 | 90.42 | 99.94 | 84.49 |
| 5 | 99.95 | 91.05 | | |
| 5.50 | | | 99.93 | 85.47 |
| 10.50 | | | 99.92 | 86.90 |

TABLE I-continued

|  | EXAMPLE 1 (1.5% Pd-3.0% Ag) | | EXAMPLE 2 (2.7% Pt-1.8% Cu) | |
|---|---|---|---|---|
| DURATION (h) | conversion % | selectivity mol % | conversion % | selectivity mol % |
| 12 | 99.97 | 92.18 | | |
| 18.50 | | | 99.89 | 88.13 |
| 20 | 100 | 92.86 | | |
| 36 | 100 | 93.68 | | |
| 38.50 | | | 99.76 | 89.82 |
| 52 | 100 | 93.70 | | |
| 54.50 | | | 99.54 | 90.84 |
| 75 | 100 | 93.97 | | |
| 77.50 | | | 98.53 | 90.69 |
| 99 | 99.95 | 94.89 | | |
| 101.50 | | | 95.35 | 92.99 |
| 123 | 99.95 | 94.83 | | |
| 125.50 | | | 85.54 | 93.51 |
| 131 | 99.95 | 94.00 | | |
| 133.50 | | | 79.94 | 94.10 |
| 141.50 | | | 72.96 | 94.45 |
| 154 | 99.32 | 95.05 | | |
| 178 | 97.00 | 96.28 | | |
| 186 | 95.18 | 96.51 | | |

Comparing the results obtained it is observed that, under the same operating conditions and with catalysts comprising the same atomic quantity of metals from groups VIII and IB, respectively, the catalyst used in Example 1 (in accordance with the invention), comprising palladium and silver, is markedly more selective to begin with than the catalyst based on platinum and copper used in Example 2 (not in accordance with the invention). Moreover, the Pt—Cu catalyst required more than 40 h of operation before the selectivity for propylene reached 90%, whereas with the Pd—Ag catalyst a selectivity of 90% was reached after only 3.50 h.

A comparison of the degrees of conversion, moreover, shows that the Pd—Ag catalyst used in Example 1 proves more stable over time than the Pt—Cu catalyst of Example 2.

Example 3 (in accordance with the invention)

A catalyst comprising 0.5% by weight of Pd and 0.5% by weight of Ag relative to the weight of active charcoal employed was prepared using the same support and a procedure similar to that described in Example 1.

3.61 g (7.50 cm³) of this catalyst were introduced into a reaction tube (internal diameter=0.8 cm). The reactor containing the catalyst was subsequently fed at a rate of 2.6 l/h (s.t.p.) with 1,2-dichloropropane and with 10.3 l/h (s.t.p.) of hydrogen at 350° C. under 1.5 bar. The residence time was assessed as being 1.4 s.

After various intervals of time, the degree of conversion of 1,2-dichloropropane and the selectivities for propylene and propane (defined as the molar fractions of 1,2-dichloropropane reacted which are converted to propylene and to propane, respectively) were measured. The results of these measurements are reproduced in Table II.

Example 4 (not in accordance with the invention)

1,2-dichloropropane was converted under the same operating conditions as those described in Example 3, but using 3.53 g (7.50 cm³) of a catalyst comprising 1% by weight of Pt and 0.5% by weight of Ag relative to the weight of active charcoal employed. This catalyst was applied to the same support and under the same operating conditions as in Example 1, using an aqueous solution of $H_2PtCl_6 \cdot 6H_2O$.

After various intervals of time, the degree of conversion of 1,2-dichloropropane and the selectivities for propylene and propane were measured. The results of these measurements are likewise reproduced in Table II.

Example 5 (not in accordance with the invention)

1,2-dichloropropane was converted under the same operating conditions as those described in Example 3, but using a catalyst comprising 1% by weight of Pt and 0.3% by weight of Cu relative to the weight of active charcoal employed. This catalyst was applied to the same support and under the same operating conditions as in Example 1, using aqueous solutions of $H_2PtCl_6.6H_2O$ and $CuCl_2.2H_2O$.

After various intervals of time, the degree of conversion of 1,2-dichloropropane and the selectivities for propylene and propane were measured. The results of these measurements are likewise reproduced in Table II.

TABLE II

| DURATION (h) | EXAMPLE 3 (0.5% Pd—0.5% Ag) | | | BXAMPLE 4 (1% Pt—0.5% Ag) | | | EXAMPLE 5 (1% Pt—0.3% Cu) | | |
|---|---|---|---|---|---|---|---|---|---|
| | conv. % | selectivity mol % $C_3H_6$ | $C_3H_8$ | conv. % | selectivity mol % $C_3H_6$ | $C_3H_8$ | conv. % | selectivity mol % $C_3H_6$ | $C_3H_8$ |
| 0.50 | 92.9 | 93.0 | 2.5 | | | | | | |
| 0.73 | | | | | | | 98.9 | 32.3 | 66.7 |
| 1.55 | 96.2 | 94.4 | 1.7 | | | | | | |
| 1.63 | | | | | | | 100 | 39.0 | 60.0 |
| 2.97 | | | | | | | 99.4 | 48.2 | 50.6 |
| 9.05 | | | | | | | 97.1 | 73.0 | 25.6 |
| 17.96 | | | | 100 | 59.3 | 39.2 | | | |
| 20.1 | 96.9 | 97.7 | 0.0 | 100 | 61.4 | 37.1 | | | |
| 21.05 | | | | | | | 97.6 | 87.8 | 10.6 |
| 44.72 | | | | 100 | 73.9 | 24.4 | | | |
| 46.05 | | | | | | | 97.1 | 93.1 | 5.3 |
| 50.1 | 97.1 | 98.5 | 0.0 | | | | | | |
| 70.05 | | | | | | | 97.8 | 94.6 | 3.9 |
| 74.1 | 97.2 | 98.5 | 0.0 | | | | | | |

Comparing the results obtained under the same operating conditions and with catalysts comprising the same atomic quantity of metals from groups VIII and IB respectively, the catalyst comprising palladium and silver is to begin with markedly more selective for propylene than the catalysts based on platinum and silver or copper. Under the operating conditions described above, using the Pt—Cu catalyst, more than 70 h of operation are required before the selectivity for propylene reaches 95%. At this time, the quantity of propane produced is still of the order of 4%. Employing the Pd—Ag catalyst, a selectivity for propylene of the order of 95% is reached after barely 1.55 h. The quantity of propane produced is very low right from the beginning of the reaction and becomes negligible after less than 20 h of operation.

Example 6 (in accordance with the invention)

A catalyst comprising 0.5% by weight of Pd and 0.5% by weight of Ag relative to the weight of the support employed was prepared by using a procedure analogous to that described in Example 1, but using titanium dioxide as support (grade HARSHAW No. Ti-0720T ⅛").

2.16 g (2.5 cm³) of this catalyst were introduced into a reaction tube (internal diameter=1.0 cm). The reactor containing the catalyst was subsequently fed at a rate of 0.4 l/h (s.t.p.) with 1,2-dichloropropane, with 0.8 l/h (s.t.p.) of hydrogen and with 2.7 l/h (s.t.p.) of helium at 350° C. under 1.5 bar. The residence time was assessed as being 1.5 s.

The degree of conversion of 1,2-dichloropropane was 100%, the selectivity for propylene 82% and the selectivity for chloropropenes (sum of the fractions of 1-, 2- and 3-chloropropenes) 18%.

Example 7 (in accordance with the invention)

For the conversion of 1,2,3-trichloropropane, a catalyst was employed comprising 1.5% by weight of Pd and 3% by weight of Ag relative to the weight of active charcoal, obtained as described in Example 1.

1.31 g (2.5 cm³) of this catalyst were introduced into a reaction tube (internal diameter=1.0 cm). The reactor containing the catalyst was then fed at a rate of 0.78 l/h (s.t.p.) with 1,2,3-trichloropropane, with 3.12 l/h (s.t.p.) of hydrogen and with 3.9 l/h (s.t.p.) of helium at 300° C. under 3 bar. The residence time was assessed as being 1.7 s.

The degree of conversion of 1,2,3-trichloropropane was 93% and the selectivity for propylene 99%.

Example 8 (in accordance with the invention)

In this example, a Pd—Sn catalyst was employed on a support of active charcoal.
a) Preparation of the catalyst on the support 50.0 g of active charcoal (grade NC 35 sold by CECA) having a pore volume of 0.5 ml/g were introduced into a round-bottomed flask with 18.0 ml of water and 17.0 ml of a solution containing 0.0147 g of Pd/ml (solution of $PdCl_2$ in 6M HCl). After a period of 60 minutes at room temperature, the impregnated active charcoal was dried under vacuum, initially at 80° C. and then at 100° C. After cooling to room temperature, 16.08 ml of a solution containing 0.0171 g of Sn/ml (aqueous solution of $SnCl_4.5H_2O$) were introduced into the flask. After a period 60 minutes at room temperature, the impregnated active charcoal was dried under vacuum, first at 80° C. and then at 100° C. The impregnated and dried active charcoal was then treated for 4 h at 350° C. with hydrogen. The catalyst thus obtained comprised 0.5% by weight (4.7 mmol) of Pd and 0.55% by weight (4.6 mmol) of Sn relative to the weight of active charcoal employed.
b) Conversion of 1,2-dichloropropane 4.5 g (10 cm³) of the catalyst described above were introduced into a reaction tube (internal diameter=0.8 cm). The reactor containing the catalyst was then fed at a rate of 3.0 l/h (s.t.p.) with 1,2-dichloropropane, with 21.0 l/h (s.t.p.) of helium and with 6 l/h (s.t.p.) of hydrogen at 300° C. under 3 bar for several hours. The residence time was assessed as being 1.7 s.

After 8.5 hours and 14.5 hours of operation, a sample of the products leaving the reactor was taken and was analysed by gas chromatography, and the degree of conversion of 1,2-dichloropropane and the selectivity for propylene were measured. The results of the measurements are reproduced in Table III. It can be seen in this table that the degree of conversion is greater than or equal to 95% and that the selectivity for propylene is 96% and that, after 14.5 hours of operation, the catalyst is still as active and selective as after 8.5 hours of operation.

Examples 9 and 10 (not in accordance with the invention)

1,2-dichloropropane was converted under the same operating conditions as those described in Example 8, but employing catalysts comprising 1% by weight of Pt and 0.3% by weight of Cu (Example 9) and 0.5% by weight of Pt and 0.3% by weight of Sn (Example 10), the contents being expressed relative to the weight of active charcoal. These catalysts were applied to the same support and under the same operating conditions as in Example 8, using aqueous solutions of $H_2PtCl_6.6H_2O$, $CuCl_2.2H_2O$ and $SnCl_4.5H_2O$.

After intervals of time of 8.5 hours and 14.5 hours, the degree of conversion of 1,2-dichloropropane and the selectivity for propylene were measured as in Example 8. The results of these measurements are likewise reproduced in Table III.

Examples 11, 12 and 13 (in accordance with the invention)

1,2-dichloropropane was converted under the same operating conditions as those described in Example 8, but employing a catalyst comprising 0.5% by weight of Pd and 0.97% by weight of Pb (Example 11), 0.5% by weight of Pd and 0.96% by weight of Tl (Example 12), and 0.5% by weight of Pd and 0.98% by weight of Bi (Example 13), the contents being expressed relative to the weight of active charcoal. These catalysts were applied to the same support and under the same operating conditions as in Example 8, using aqueous solutions of $Pb(CH_3CO_2)_2.3H_2O$, $Tl(CH_3CO_2)_3$ and $Bi(NO_3)_3.5H_2O$.

After intervals of 8.5 hours and 14.5 hours, the degree of conversion of 1,2-dichloropropane and the selectivity for propylene were measured as in Example 8. The results of these measurements are likewise reproduced in Table III.

TABLE III

| EX. | CATALYST | After operation for 8.5 h | | After operation for 14.5 h | |
|---|---|---|---|---|---|
| | | conversion % | selectivity mol % | conversion % | selectivity mol % |
| 8 | Pd-Sn/C | 95 | 96 | 96 | 96 |
| 9 | Pt-Cu/C | 98 | 61 | 99 | 81 |
| 10 | Pt-Sn/C | 99 | 58 | 98 | 77 |
| 11 | Pd-Pb/C | 96 | 94 | 96 | 97 |
| 12 | Pd-Tl/C | 90 | 98 | 97 | 97 |
| 13 | Pd-Bi/C | 91 | 96 | 86 | 97 |

Comparing the results obtained, it is observed that, under the same operating conditions, the catalysts used in Examples 8, 11, 12 and 13 (in accordance with the invention), comprising palladium, make it possible to obtain a very good conversion of 1,2-dichloropropane, while at the same time being markedly more selective with respect to propylene than the platinum-based catalysts used in Examples 9 and 10 (not in accordance with the invention).

Example 14 (in accordance with the invention)

In this example, Pd—Sn catalyst was employed on an alumina support.

The catalyst was prepared under the same operating conditions as in Example 8, employing an alumina support (alpha-alumina having a pore volume of 0.43 ml/g and a specific surface area of 3 m²/g).

1,2-dichloropropane is converted under the same operating conditions as those described in Example 8, but using 9.1 g (10 cm³) of a catalyst comprising 0.5% by weight of Pd and 0.55% by weight of Sn relative to the weight of alumina.

After intervals of 8.5 hours and 14.5 hours, the degree of conversion of 1,2-dichloropropane and the selectivity for propylene were measured as in Example 8. The results of these measurements are reproduced in Table IV.

Example 15 (not in accordance with the invention)

1,2-dichloropropane was converted under the same operating conditions as those described in Example 14, but employing a catalyst comprising 0.5% by weight of Pt and 0.3% by weight of Sn relative to the weight of alumina. This catalyst was applied to the same support and under the same operating conditions as in Example 14, using an aqueous solution of $H_2PtCl_6.6H_2O$.

After the same intervals of time, the degree of conversion of 1,2-dichloropropane and the selectivity for propylene were measured as in Example 14. The results of these measurements are likewise reproduced in Table IV.

TABLE IV

| EX. | CATALYST | After operation for 8.5 h | | After operation for 14.5 h | |
|---|---|---|---|---|---|
| | | conversion % | selectivity mol % | conversion % | selectivity mol % |
| 14 | Pd-Sn/Al₂O₃ | 68 | 97 | 61 | 97 |
| 15 | Pt-Sn/Al₂O₃ | 66 | 88 | 54 | 78 |

Comparing the results obtained, it is observed that, under the same operating conditions, the catalyst used in Example 14 (in accordance with the invention), comprising palladium, is markedly more selective with respect to propylene than the platinum-based catalyst used in Example 15 (not in accordance with the invention).

What is claimed is:

1. A process for converting a chlorinated alkane of the formula $C_nH_{2n+2-x}Clx$ in which n is an integer from 2 to 6 and x is an integer from 1 to (2n+2) into at least one less chlorinated alkene by reacting the chlorinated alkane with hydrogen in the presence of a catalyst on a support, said catalyst comprising palladium and a metal M selected from the group consisting of silver, gallium, indium, thallium, germanium, tin, lead, arsenic, antimony, bismuth and mixtures thereof.

2. The process according to claim 1, wherein the metal M is selected from silver, tin, lead, thallium and bismuth.

3. The process according to claim 2, wherein the metal M is tin or silver.

4. The process according to claim 1, wherein the chlorinated alkane is chosen from chloropropanes.

5. The process according to claim 4, wherein the chloropropanes are by-products formed in the production of allyl chloride and/or epichlorohydrin.

6. The process according to claim 4, wherein the chlorinated alkane is 1,2-dichloropropane.

7. The process according to claim 1, wherein the support is active charcoal.

8. The process according to claim 1, wherein the quantity of palladium on the support is from 0.05% to 10% by weight relative to the weight of the support.

9. The process according to claim 1, wherein the quantity of metal M on the support is from 0.05% to 10% by weight relative to the weight of the support.

10. The process according to claim 1, wherein the ratio by weight of palladium to the metal M is from 0.05 to 20.

11. The process according to claim 1, wherein the reaction is carried out at a temperature of from 150° to 450° C. under a pressure of from 1 to 30 bar.

12. The process according to claim 1, wherein the molar ratio of hydrogen to chlorinated alkane is from 0.1 to 40.

13. The process according to claim 1, wherein the reaction is carried out in the gaseous phase with a mean contact time between the gases employed and the catalyst of from 0.5 to 30 seconds.

14. The process according to claim 1, wherein said support is active charcoal, said palladium on said active charcoal support is from 0.05% to 10% by weight relative to the weight of the support, said metal M is tin or silver, said metal M on said active charcoal support is from 0.05% to 10% by weight relative to the weight of the support, the ratio by weight of palladium to the metal M is from 0.05 to 20, and said chlorinated alkane is 1,2-dichloropropane.

15. The process according to claim 1, wherein the reaction is carried out in the gaseous phase at a temperature of from 150° to 450° C. under a pressure of from 1 to 30 bar, with a mean contact time between the gases employed and the catalyst of from 0.5 to 30 seconds, and a molar ratio of hydrogen to chlorinated alkane of from 0.1 to 40.

16. A process for converting a chlorinated alkane into at least one less chlorinated alkene by reacting the chlorinated alkane with hydrogen in the presence of a catalyst on a support, said catalyst consisting of palladium and a metal M selected from the group consisting of silver, gallium, indium, thallium, germanium, tin, lead, arsenic, antimony, bismuth and mixtures thereof.

17. The process according to claim 16, wherein said support is active charcoal, said palladium on said active charcoal support is from 0.05% to 10% by weight relative to the weight of the support, said metal M is tin or silver, said metal M on said active charcoal support is from 0.05% to 10% by weight relative to the weight of the support, the ratio by weight of palladium to the metal M is from 0.05 to 20, and said chlorinated alkane is 1,2-dichloropropane.

18. The process according to claim 16, wherein the reaction is carried out in the gaseous phase at a temperature of from 150° to 450° C. under a pressure of from 1 to 30 bar, with a mean contact time between the gases employed and the catalyst of from 0.5 to 30 seconds, and a molar ratio of hydrogen to chlorinated alkane of from 0.1 to 40.

* * * * *